United States Patent [19]

Obikawa

[11] Patent Number: 5,061,400

[45] Date of Patent: Oct. 29, 1991

[54] LIQUID CRYSTAL COMPOUNDS

[75] Inventor: Tsuyoshi Obikawa, Nagano, Japan

[73] Assignee: Seiko Epson Corporation, Tokyo, Japan

[21] Appl. No.: 371,909

[22] Filed: Jun. 27, 1989

[30] Foreign Application Priority Data

| | | | |
|---|---|---|---|
| Jul. 5, 1988 | [JP] | Japan | 63-168039 |
| Jul. 19, 1988 | [JP] | Japan | 63-180870 |
| Nov. 26, 1988 | [JP] | Japan | 63-299036 |
| Feb. 23, 1989 | [JP] | Japan | 1043479 |

[51] Int. Cl.$^5$ .................... C09K 19/30; C09K 19/52; C09K 19/12; C07C 255/00

[52] U.S. Cl. .................... 252/299.63; 252/299.01; 252/299.66; 252/299.67; 558/431

[58] Field of Search .................... 252/299.62, 299.63, 252/299.64, 299.65, 299.66; 558/299.01, 431

[56] References Cited

FOREIGN PATENT DOCUMENTS

| | | |
|---|---|---|
| 3631415 | 3/1988 | Fed. Rep. of Germany . |
| WO8802130 | 3/1988 | World Int. Prop. O. . |

OTHER PUBLICATIONS

Chan, et al., Mol. Cryst. Liq. Cryst., 185, vol. 123, pp. 185–204.

Balkwill, et al., Mol. Cryst. Liq. Cryst., 1985, vol. 123, pp. 1–13.

Kelly, et al., Mol. Cryst. Liq. Cryst., 1984, vol. 110, pp. 239–261.

Kelly, et al., Helvetica Chimica Acta, 1985, vol. 68, pp. 1444–1452.

Fearon, et al., Mol. Cryst. Liq. Cryst., 1985, vol. 124, pp. 89–103.

Kelly, Helvetica Chimica Acta, vol. 67, 1984, pp. 1572–1579.

Kelly, et al., Helvetica Chimica Acta, vol. 68, 1985, pp. 813–817.

*Primary Examiner*—John S. Maples

*Assistant Examiner*—Shean C. Wu

*Attorney, Agent, or Firm*—Blum Kaplan

[57] ABSTRACT

2′-fluoro-4″-trans-cyclohexyl-terphenyl derivatives represented by the general formula:

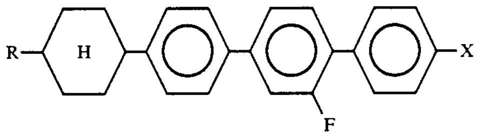

wherein the cyclohexyl is the trans isomer, R is a straight chain alkyl having from 1 to 12 carbon atoms, X is a straight chain alkyl having from 1 to 12 carbon atoms, a straight chain alkoxy having from 1 to 12 carbon atoms or —CN and the compounds exhibit the nematic phase. The fluoro-cyclohexyl-terphenyl derivatives have a low crystal-nematic phase transition temperature (C-N point), a high nematic phase-isotropic liquid phase transition temperature (N-I point) and low viscosity and may be included in liquid crystal compositions for improved display devices having a wide temperature range, a low driving voltage and a rapid response speed.

11 Claims, No Drawings

LIQUID CRYSTAL COMPOUNDS

BACKGROUND OF THE INVENTION

This invention relates to 2'-fluoro-4"-trans-cyclohexyl-terphenyl derivatives, and more particularly to novel liquid crystal compositions including 2'-fluoro-4"-trans-cyclohexyl-terphenyl suitable for use in electro-optical displays.

Liquid crystal display devices utilize electro-optical effects possessed by liquid crystals. The liquid crystals used in these devices include a nematic phase, a cholesteric phase and a smectic phase. The most widely used display mode uses liquid crystals in the nematic phase and include a twisted nematic type (TN type), a dynamic scattering type, a guest-host type, and the like.

Liquid crystal display devices have several advantages, including for example, their small size and ability to be made thin; the device can be driven at low voltage with low power consumption; the liquid crystal is a light receiving elements, when a liquid crystal display is viewed over a long time period, eye strain does not occur.

Thus, liquid crystal display technology has been applied to watches, electronic counters, audio equipment and automobile dash board indicators, and the like. More particularly, liquid crystal devices have also been applied recently to personal computers and word processor displays and to other displays requiring high resolution and many pixels, including black and white and color pocket televisions, and the like. Thus, liquid crystal display devices have attracted attention as potentially replacing cathode ray tubes. As a result, liquid crystal display devices have been applied in various areas and it is likely that the use will be broadened further.

For practical use, liquid crystal compositions must possess the following characteristics:

1. Liquid crystal must be colorless and thermally, optically, electrically and chemically stable;
2. Have a wide temperature range and a wide viewing angle;
3. A rapid electro-optical response speed;
4. Require a low driving voltage;
5. A steep rise in voltage-light transmittance; and
6. The temperature dependency of threshold voltage be small; and,
7. A wide visual angle.

Many liquid crystals have one of the above desired properties, however, no compound satisfying more than one property is known. Thus, liquid crystal compositions are formed of several different nematic liquid crystal compounds or liquid crystal compositions are obtained by mixing liquid crystal compounds with non-liquid crystal compounds to obtain the desirable properties.

In general, a composition including a liquid crystal compound having a relatively low molecular weight and having C-N point (or melting point) at about room temperature and a liquid crystal compound having a high molecular weight and having C-N point higher than 200.C is used. In order to satisfy property 2, a liquid crystal compound having an N-I point as high as possible and a N-I point as low as possible is required. However, conventional liquid crystal compounds having an N-I point higher than 200° C. do not have an N-I point higher than 250° C., while their C-N point is relatively low, as shown in Table 1.

Conventional liquid crystal compounds having a high N-I point also have high viscosity. Thus, these liquid crystal compounds tend to increase the viscosity of the liquid crystal composition obtained by mixing them, resulting in a delay in the response speed of the liquid crystal display devices. In order to decrease the driving voltage of a liquid crystal display device, it is necessary to reduce the threshold voltage. However, the following relationship exists between threshold voltage (Vth), elasticity constant (K) and dielectric constant anisotropy ($\Delta\epsilon$):

$$Vth \propto \left[\frac{K}{\Delta\epsilon}\right]^{\frac{1}{2}}$$

Thus, in order to decrease $V_{th}$, a liquid crystal compound having large $\Delta\epsilon$ and small K is required. However, conventional compounds having a high N-I point and large $\Delta\epsilon$ have a very large elasticity constant which results in an adverse increase in $V_{th}$.

| Liquid Crystal Compound | C—N Point (°C.) | N—I Point (°C.) |
|---|---|---|
| 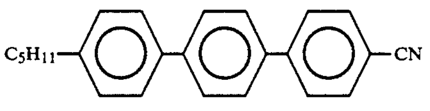 | 130 | 239 |
| 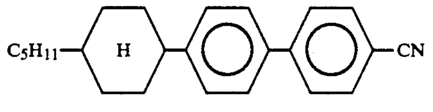 | 94 | 219 |
| 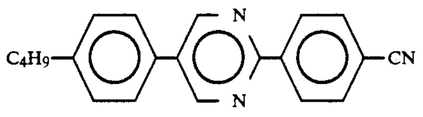 | 94.7 | 246.7 |

-continued

| Liquid Crystal Compound | C—N Point (°C.) | N—I Point (°C.) |
|---|---|---|
| 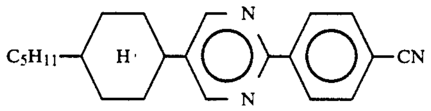 | 100.5 | 231 |

Accordingly, it is desirable to provide an improved liquid crystal material having a low C-N point, a high N-I point and a low viscosity.

SUMMARY OF THE INVENTION

2'-fluoro-4''-trans-cyclohexyl-terphenyl derivatives represented by the general formula:

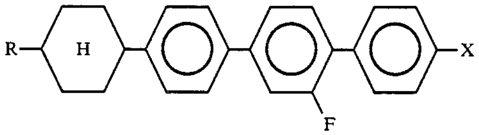

wherein the cyclohexyl is the trans isomer, R is a straight chain alkyl having from 1 to 12 carbon atoms, X is a straight chain alkyl having from 1 to 12 carbon atoms, a straight chain alkoxy having from 1 to 12 carbon atoms or —CN and the compounds exhibit the nematic phase.

The 2'-fluoro-4''-trans-cyclohexyl-terphenyl derivatives in accordance with the invention have a low crystal-nematic phase transition temperature (C-N point), a high nematic phase-isotropic liquid phase transition temperature (N-I point) and a low viscosity. The 2'-fluoro-4''-trans-cyclohexyl-terphenyl derivatives may be mixed with other liquid crystal compounds to obtain liquid crystal display devices having a wide temperature range, a low driving voltage and a rapid response speed.

Accordingly, it is an object of the invention to provide an improved liquid crystal compound.

It is another object of the invention to provide 2'-fluoro-4''-trans-cyclohexyl-terphenyl derivatives.

It is a further object of the invention to provide 2'-fluoro-4''-trans-cyclohexyl-terphenyl derivatives suitable for use as ingredients in liquid crystal compositions utilized as electro-optical display materials.

Still another object of the invention is to provide liquid compositions including 2'-fluoro-4''-trans-cyclohexyl-terphenyl derivatives crystal materials suitable for use in TN cells.

Still a further object of the invention is to provide improved liquid crystal compositions including 2'-fluoro-4''-trans-cyclohexyl-terphenyl derivatives for improving the temperature range, driving voltage and response speed.

Yet a further object of the invention is to provide a method for preparing improved 2'-fluoro-4''-trans-cyclohexyl-terphenyl derivatives.

Yet another object of the invention is to provide improved liquid crystal display devices including the liquid crystal compositions including 2'-fluoro-4''-trans-cyclohexyl-terphenyl derivatives.

Still other objects and advantages of the invention will in part be obvious and will in part be apparent from the specification.

The invention accordingly comprises the several steps and the relation of one or more of such steps with respect to each of the others thereof, which will be exemplified in the composition method and device hereinafter disclosed, and the scope of the invention will be indicated in the claims.

DESCRIPTION OF THE PREFERRED EMBODIMENTS

The liquid crystal compounds prepared in accordance with the invention are 2'-fluoro-4''-trans-cyclohexyl-terphenyl derivatives represented by the general formula as follows:

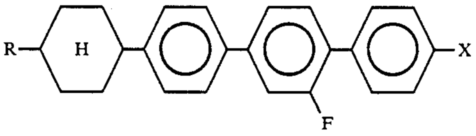
[1]

wherein the cyclohexyl is the trans isomer, R is a straight chain alkyl having from 1 to 12 carbon atoms, X is a straight chain alkyl having from 1 to 12 carbon atoms, a straight chain alkoxy having from 1 to 12 carbon atoms or —CN and the compounds exhibit the nematic phase. Preferably, X is —CN and R is an alkyl having 1 to 7 carbon atoms. When the number of carbon atoms exceeds about 7, the response speed is reduced, the dielectric anisotropy ($\Delta\epsilon$) increases and voltage increases.

The 2'-fluoro-4''-trans-cyclohexyl-terphenyl compounds of this invention represented by the following general formulae II to IV have a low crystal-nematic phase transition temperature (C-N point), a high nematic phase-isotropic liquid transition temperature (N-I point), positive large dielectric anisotropy ($\Delta\epsilon$) and low viscosity.

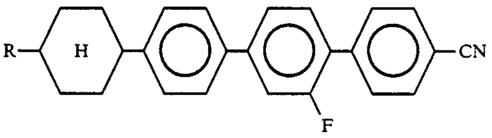
[II]

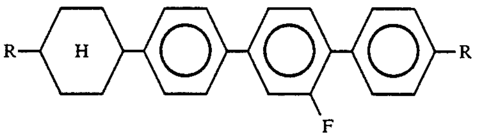
[III]

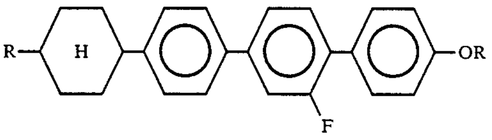
[IV]

The terpheny derivatives wherein X is a cyano group can be produced by the following reaction scheme:

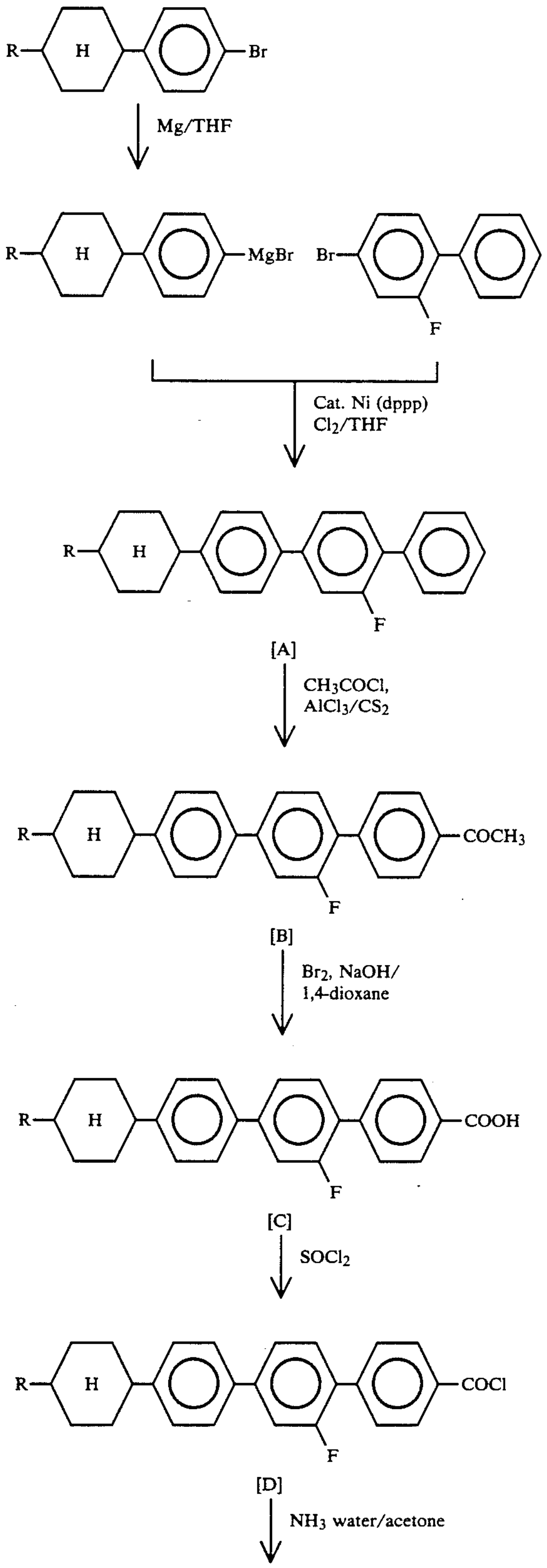

-continued

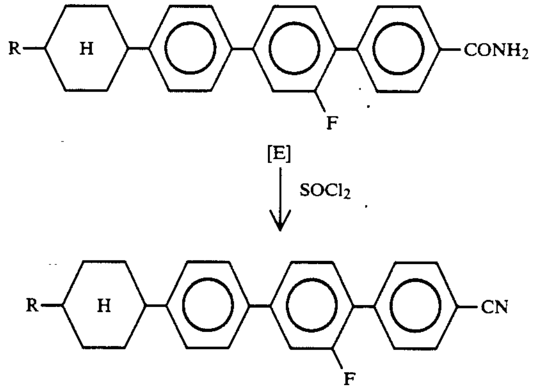

[II]

As a catalyst, "Ni(dppp)cl2" is represented by the formula as follows:

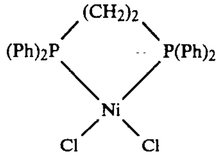

In a stream of nitrogen gas, 4'-cyclohexyl-4-phenylbromide is reacted with magnesium. Dehydrated tetrahydrofuran (THF) and iodine are added as catalysts to prepare a Grignard reagent. In a stream of nitrogen gas, the Grignard reagent is coupled with 4-bromo-2-fluorobiphenyl in the presence of $Ni(dppp)Cl_2$ acting as a catalyst to produce compound [A]. In a solvent of carbon disulfide, Compound [A] and acetyl chloride are subjected to a Friedel-Crafts reaction using anhydrous aluminum chloride as a catalyst to yield Compount [B].

An aqueous solution of sodium hypobromite (NaOBr) is prepared with bromine and an aqueous solution of sodium hydroxide or a commercially available aqueous solution of sodium hypochlorite (NaOCl). The aqueous solution of sodium hypobromite and Compound [B] are subjected to a haloform reaction in a solvent of 1,4-dioxane to yield Compound [C]. Compound [C] is chlorinated with thionyl chloride to yield Compound [D]. Compound [D] is reacted in acetone with ammonia water to yield Compound [E].

Compound [E] is dehydrated with thionyl chloride phosphorus oxychloride or the like to yield a novel liquid crystal compound in accordance with the invention.

The terphenyl derivatives wherein X is a straight chain alkyl can be produced by the following reaction scheme.

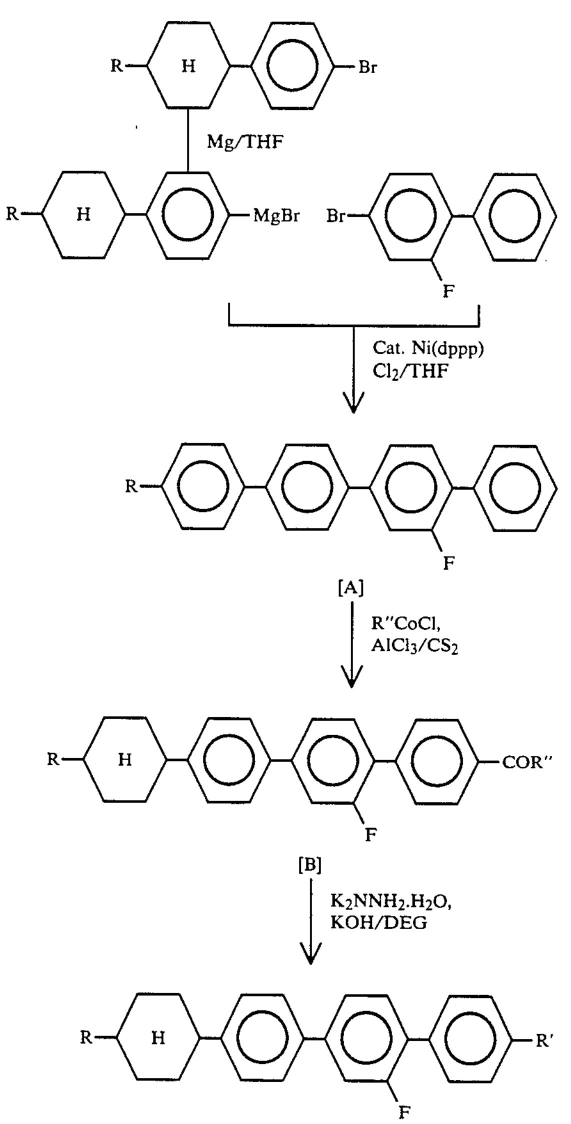

[III]

In a stream of nitrogen gas, 4'-alkyl-4-cyclohexylphenylbromide is reacted with magnesium. Dehydrated tetrahydrofuran (THF) and iodine are added as catalysts to prepare a Grignard reagent. In a stream of nitrogen gas, the Grignard reagent is coupled with 4-bromo-2-fluorobiphenyl in the presence of Ni(dppp)$Cl_2$ acting as a catalyst to produce Compound [A]. In a solvent of carbon disulfide, with anhydrous aluminum chloride as a catalyst, Compound [A] and an acyl chloride are subjected to a Friedel-Crafts reaction to yield Compound [B']. With hydrated hydrazine and potassium hydroxide in diethylene glycol, Compound [B'] is reduced by a Walff-Kischner reaction to yield the Compound (III) in accordance with the invention. The terphenyl derivatives wherein X is a straight chain alkoxy are produced by the following reaction scheme.

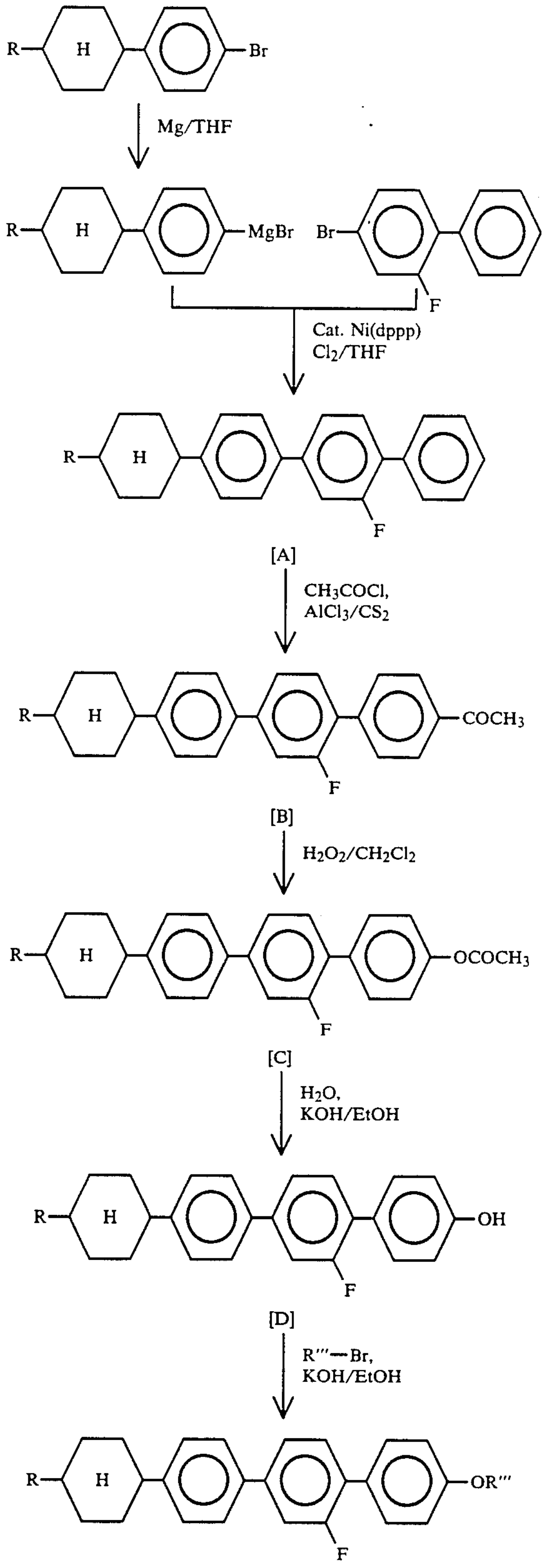

[IV]

In a stream of nitrogen gas, 4'-alkyl-4-cylcohexyl phenylbromide is reacted with magnesium. Dehydrated tetrahydrofuran (THF) and iodine are added as catalysts to prepare a Grignard reagent. In a stream of nitrogen gas, the Grignard reagent is coupled with 4-bromo-2-fluorobiphenyl in the presence of Ni(dppp)$Cl_2$, acting as a catalyst, to produce Compound [A]. In a solvent of carbon disulfide, Compound [A] and acetyl chloride are subjected to a Friedel-Crafts reaction using anhydrous aluminum chloride as a catalyst to yield Compound [B].

Compound [B] is subjected to a Bayer-Filliger oxidation with hydrogen peroxide in methylene chloride to yield Compound [C'']. Compound [C''] is hydrolyzed with a potassium hydroxide aqueous solution in ethanol to yield Compound [D'']. Compound [D''] is refluxed in ethanol with a bromoalkane and potassium hydroxide to yield a liquid crystal compound [IV] in accordance with the invention.

The following Examples are set forth by way of illustration to show preparation of the terphenyl derivatives in accordance with the invention. They are set forth for purposes of illustration only, and not intended in a limiting sense.

EXAMPLE 1

Production of 4''-(trans-4'''-pentylcyclohexyl)-2'-fluoro-4-cyanoterphenyl [Compound (I) wherein R is $C_5H_{11}$]:

Step 1

In a stream of $N_2$, 3.2 g of magnesium flakes were warmed and stirred to activate the magnesium and 0.12 g of iodine and 40 $cm^3$ of THF were added. A solution of 20 g of 4-(trans-4'-pentylcyclohexyl)bromobenzene in 100 $cm^3$ of THF was added drop-wise to the mixture. After completion of the drop-wise addition, the mixture was stirred at 50° C. for 3 hours to prepare a THF solution of 4-(trans-4'-pentylcyclohexyl)phenyl magnesium bromide.

Step 2

The THF solution of 4-(trans-4'-pentylcyclohexyl) phenyl magnesium bromide was filtered in a stream of $N_2$ and a solution of 16.3 g of 4-bromo-2-fluorobiphenyl and 7 mg of Ni(dppp)$Cl_2$ in 40 $cm^3$ of THF was added drop-wise over 2 hours. After completion of the addition, the mixture was refluxed for 64 hours. The reaction liquid was cooled and 100 $cm^3$ of 10% hydrochloric acid was added. The mixture was extracted with chloroform and washed sequentially with 10% hydrochloric acid and water. After distilling chloroform off, the residue was treated through a silica gel column using chloroform solvent to yield 17.2 g of 4-(trans-4'''-pentylcyclohexyl)-3'-fluoroterphenyl.

Step 3

7.5 g of powdered anhydrous aluminum chloride was dispersed in 65 $cm^3$ of carbon disulfide and 4.1 g of acetyl chloride was added drop-wise while stirring. Next, the mixture was cooled below 0° C. in a salt-ice bath. While stirring, a solution of 17.2 g of 4-(trans-4'''-pentylcyclohexyl)-3'-fluoroterphenyl in 130 $cm^3$ of carbon disulfide was added drop-wise to the mixture. After completion of the drop-wise addition, stirring was continued below 0° C. for 2 hours. The reaction mixture was poured onto hydrochloric acid and ice water. After carbon disulfide was subjected to steam distillation, the aqueous phase was extracted with chloroform and washed with 10% hydrochloric acid and water. After distilling chloroform off, the residue was recrystallized from a solvent mixture of chloroform and acetone to yield 15.8 g of 4-acetyl-2'-fluoro-4''-(trans-4'''-pentylcyclohexyl)terphenyl.

Step 4

15.8 g of 4-Acetyl-2'-fluoro-4''-(trans-4'''-pentycyclohexyl)-terphenyl was heated and dissolved in 200 $cm^3$ of 1,4-dioxane. The solution was quenched to precipitate fine crystals. The mixture was cooled below 5° C. in an ice water bath and an aqueous solution of sodium hypobromite aqueous solution prepared from 22.8 g of $Br_2$ and 14.3 g of sodium hydroxide was added drop-wise while vigorously stirring. After the drop-wise addition was completed the mixture was stirred for an hour below 5° C. and for an hour at 40° C. An effective amount of 10% Hydrochloric acid was added to the reaction liquid to precipitate crystals. The crystals were filtered and thoroughly washed with water. The crystals were recrystallized from ethanol to yield 14.3 g of 2'-fluoro-4''-(trans-4'''-pentylcyclohexyl)terphenyl-4-carboxylic acid.

Step 5

14.3 g of 2'-Fluoro-4''-(trans-4'''-pentylcyclohexyl) terphenyl-4-carboxylic acid was refluxed for 5 hours with 23 $cm^3$ of thionyl chloride. An excess of thionyl chloride was distilled off under reduced pressure by an aspirator. Next, the residue was dissolved in 20 $cm^3$ of toluene and toluene was distilled off under reduced pressure by an aspirator. The residue was recrystallized from hexane to yield 12.6 g of 4-chloroformyl-2'-fluoro-4''-(trans-4'''-pentylcyclohexyl)terphenyl.

Step 6

12.6 g of 4-chloroformyl-2'-fluoro-4''-(trans-4'''-pentylcyclohexyl)terphenyl was dissolved in 50 $cm^3$ of acetone. 27 $cm^3$ of concentrated ammonia water cooled below 5° C. on an ice water bath was drop-wise added to the solution while stirring vigorously. The crystals formed were filtered and washed with water until the ammonia odor was lost. The crystals were dried at 80° C. to yield 11.4 g of 4-amido-2'-fluoro-4''-(trans-4'''-pentylcyclohexyl)terphenyl.

Step 7

11.4 g of 4-amido-2'-fluoro- 4''-(trans-4'''-pentylcyclohexyl)terphenyl was refluxed with 37 $cm^3$ of thionyl chloride for 20 hours. An excess of thionyl chloride was distilled off under reduced pressure by an aspirator. The residue was recrystallized from a solvent mixture of chloroform and hexane to give 8.7 g of 4-cyano-2'-fluoro-4''-(trans-4'''-pentylcyclohexyl) terphenyl. This compound was analyzed by gas chromatography and showed 99.8%. Further according to DSC measurement, the phase transition temperature of this compound was as follows.

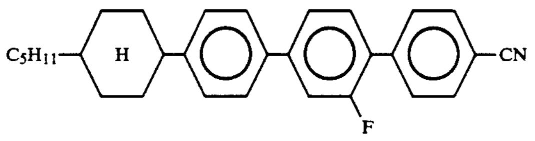

$C_1 \xrightarrow{98^\circ \text{ C.}} C_2 \xrightarrow{133^\circ \text{ C.}} N \xrightarrow{353^\circ \text{ C.}} I$ wherein $C_1$ and $C_2$ represent the crystal phase, N represents the nematic phase and I represents an isotropic liquid

EXAMPLE 2

4-cyano-2'-fluoro-4"-(trans-4'"-propylcyclohexyl)terphenyl prepared in the same manner as 4"-(trans-4'"-pentylcyclohexyl)-2'-fluoro-4-cyanoterphenyl in Example 1. The phase transition temperatures were as follows:

$$C \xrightarrow{153^\circ C.} N \xrightarrow{369^\circ C.} I$$

EXAMPLE 3

4-cyano-2'-fluoro-4"-(trans-4'"-butylcyclohexyl)terphenyl was prepared in the same manner as 4"-(trans-4'"-pentylcyclohexyl)- 2'-fluoro-4-cyanoterphenyl in Example 1. The phase transition temperatures were as follows:

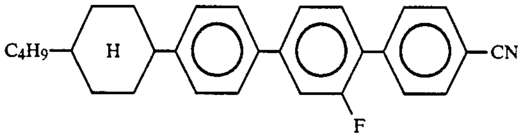

$$C \xrightarrow{141^\circ C.} S \xrightarrow{143^\circ C.} N \xrightarrow{359^\circ C.} I$$

wherein S represents smectic phase; and C, N and I have the same meaning as in Example 1.

Further phase transition temperatures in Examples 1 through 3 are summarized in Table 2.

TABLE 2

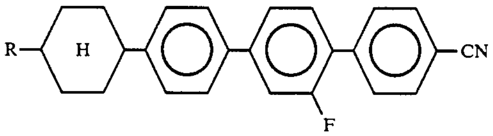

(unit °C.)

| R | $C_1$ | $C_2$ | S | N.I |
|---|---|---|---|---|
| $C_3H_7$ | | 153 | — | 369 |
| $C_4H_9$ | — | 141 | 143 | 359 |
| $C_5H_{11}$ | 98 | 133 | — | 353 |

EXAMPLE 4

Production of 4"-(trans-4'"-propylcyclohexyl)-4-propylterphenyl [Compound (I) wherein R is $C_5H_{11}$ and X is $C_3H_7$]:

Step 1

In a stream of $N_2$, 3.2 g of magnesium flakes were warmed and stirred to activate the magnesium. A solution of 0.12 g of iodine, 40 $cm^3$ of THF and 20 g of 4-(trans-4'-pentylcyclohexyl bromobenzene in 100 $cm^3$ of THF was added drop-wise to the magnesium. The mixture was stirred at 50° C. for 3 hours to prepare a Grignard reagent.

Step 2

The grignard reagent prepared in Step 1 was filtered in a stream of $N_2$ and a solution of 16.3 g of 4-bromo-2-fluorobiphenyl and 7 mg of $Ni(dppp)Cl_2$ in 40 $cm^3$ of THF was added dropwise. The mixture was refluxed for 64 hours. The reaction liquid was cooled and 100 $cm^3$ of 10% hydrochloric acid was added. The mixture was extracted with chloroform and washed sequentially with 10% hydrochloric acid and with water. After distilling chloroform off, the residue was treated through a silica gel column using chloroform solvent to yield 15.5 g of 4-(trans-4'"-pentylcyclohexyl)-3'-fluoroterphenyl.

Step 3

6.8 g of powdered anhydrous aluminum chloride was dispersed in 60 $cm^3$ of carbon disulfide and 4.4 g of propionyl chloride was added drop-wise while stirring. While cooling and stirring below 0° C., a solution of 15.5 g of 4-(trans-4'"-pentylcyclohexyl)-3'-fluoroterphenyl in 120 $cm^3$ of carbon disulfide was added dropwise to the mixture. The mixture was stirred at 0° C. for 2 hours. The reaction mixture was poured onto hydrochloric acid and ice water. After carbon disulfide was removed by steam distillation, the aqueous phase was extracted with chloroform and washed with 10% hydrochloric acid and water. After distilling chloroform off, the residue was recrystallized from a solvent mixture of chloroform and acetone to yield 12.0 g of 4-propionyl-2'-fluoro-4"-(trans-4'"-pentylcyclohexyl)terphenyl.

Step 4

A mixture of 12.0 g of 4-propionyl-2'-fluoro-4"-(trans-4'"-pentylcyclohexyl)terphenyl, 2.7 g of hydrated hydrazine, 4.5 g of potassium hydroxide and 270 $cm^3$ of diethylene glycol was refluxed at 130° C. for one hour and at 200° C. for 7 hours. The reaction mixture was cooled and 300 $cm^3$ of water was added. The mixture was extracted with chloroform and washed with water. After distilling chloroform off, the residue was recrystallized from a solvent mixture of chloroform and acetone to yield 10.5 g of 4-propyl-4"-(trans-4'"-pentylcyclohexyl)terphenyl. As the result of DSC measurement, the phase transition temperature of this compound was as follows.

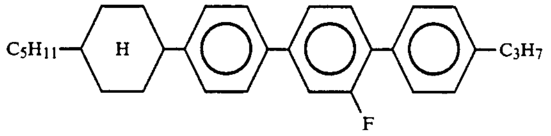

$$C \xrightarrow{66^\circ C.} S_1 \xrightarrow{167^\circ C.} S_2 \xrightarrow{242^\circ C.} N \xrightarrow{285^\circ C.} I$$

wherein C represents crystals, $S_1$ and $S_2$ represent the smectic phase, N represents the nematic phase and I represents an isotropic liquid.

Composition Example 1

Several compositions [A] were prepared by preparing compositions including from 5 to 20 wt % 4-cyano-2'-fluoro-4"-(trans-4'"-pentylcyclohexyl)terphenyl in a commercially available liquid crystal composition known as ZLI-1565 (manufactured by Merck Inc.) For purpose of comparison, Composition [B] was prepared by mixing 10 wt % 4-cyano-4"-pentylterphenyl in ZLI-1565. The C-N point, N-I point and viscosity were measured for each of the compositions.

The Compositions [A] and [B] were sealed in 8 μm TN type cells. Using the alternate static driving method, voltage-luminance characteristics at 25° C. to determine threshold voltage $V_{th}$ (voltage at 10% of light transmittance), rise and down response time $T_r$ an $T_d$, and temperature dependency T of threshold voltage (the value obtained by dividing the difference in threshold voltage between 0° C. and at 40° C. with a mean value of threshold voltages at 0° C. and 40° C.) were measured. These results are shown in Table 3.

TABLE 3

| | [A-5] | [A-10] | [A-15] | [A-20] | [B] |
|---|---|---|---|---|---|
| C-N point (°C.) | <−20 | <−20 | <−20 | −10 | <−20 |
| N-I point (°C.) | 97 | 108 | 119 | 131 | 105.5 |
| viscosity (c · p) | 17.2 | 19.6 | 22.0 | 24.3 | 20.1 |
| Vth (V) | 2.33 | 2.36 | 2.39 | 2.42 | 2.42 |
| Tr (msec) | 2.74 | 30.0 | 34.3 | 38.1 | 32.0 |
| Td (msec) | 53.8 | 58.2 | 63.0 | 67.5 | 64.7 |
| Δ T | 0.28 | 0.25 | 0.23 | 0.21 | 0.32 |

Composition Example 2

Liquid crystal compositions [C] were prepared by 4-propyl-2′-fluoro-4″-(trans-4‴-pentylcyclohexyl)-terpenyl in varying percentages of 5, 10, 15 and 20 wt % in 90 wt % of commercially available liquid crystal composition ZLI-1565 (manufactured by Merck Inc.). A comparative example [D] including 10 wt % and 4-cyano-4″-(trans-4‴-pentylcyclohexyl)biphenyl in ZLI-1565 was also prepared. The C-N point, N-I point and viscosity were measured and the results are shown in Table 4.

TABLE 4

| | [C-5] | [C-10] | [C-15] | [C-20] | [D] |
|---|---|---|---|---|---|
| C-N point (°C.) | <−20 | <−20 | <−20 | −20 | <−20 |
| N-I point (°C.) | 95 | 105 | 115 | 126 | 101 |
| viscosity (c · p) | 16.3 | 17.6 | 19.0 | 20.4 | 20.1 |

While the invention has been described in detail with reference to ZLI-1565, it is understood that the increase in N-I point and low viscosity can be obtained with other compatible liquid crystal compositions. The 2′-fluoro-4″-cyclohexyl derivatives are included in the composition in at least a minimum effective amount to increase the N-1 point and adjust the viscosity as desired up to about 20 weight percent based on the total weight of the composition. Preferably, between about 5 to 15 weight percent is added.

As described above, the 2′-fluoro-4″-trans-cyclohexyl-terphenyl derivatives in accordance with the present invention have a high N-I points and low viscosity. Liquid crystal compositions having a wide temperature range for practical use and a rapid response speed are obtained when liquid crystal compounds in accordance with the invention are mixed with conventional liquid crystal compositions. In particular, liquid crystal compositions having a low driving voltage are obtained in compounds having a cyano group at the terminal position. Thus, the terpheny derivatives prepared in accordance with the invention are extremely useful as constituent components for nematic liquid crystal compositions.

It will thus be seen that the objects set forth, among those made apparent from the preceding description, are efficiently attained and, since certain changes may be made in carrying out the above embodiments and in the compositions set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention, which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A 2′-fluoro-4-″-trans-cyclohexyl-terphenyl derivative represented by the general formula:

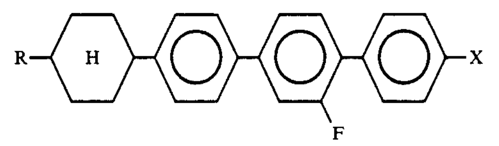

(I)

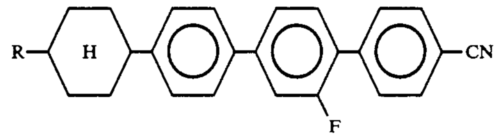

(I)

wherein R is a straight chain alkyl group having 1 to 12 carbon atoms and the cyclohexane ring is a trans isomer.

2. The 2′-fluoro-4″-trans-cyclohexyl-terphenyl derivative of claim 1, wherein R is a straight chain alkyl having 1 to 7 carbon atoms.

3. The 2′-fluoro-4″-trans-cyclohexyl-terphenyl derivative of claim 1, wherein the compound is 4″-(trans-4‴-pentylcyclohexyl)-2′-fluoro-4-cyano-terphenyl.

4. The 2′-fluoro-4″-trans-cyclohexyl-terphenyl derivative of claim 1, wherein the compound is 4-cyano-2′-fluoro′4″-(trans′4‴-propylcyclohexyl)-terphenyl.

5. The 2′-fluoro-4″-trans-cyclohexyl-terphenyl derivative of claim 1, wherein the compound is 4-cyano-2′-fluoro-4″-(trans-4‴-butylcyclohexyl)-terphenyl.

6. A nematic liquid crystal composition comprising an effective amount of at least one 2′-fluoro-4″-trans-cyclohexyl-terphenyl derivative for widening the nematic temperature range and improving the response speed, the terphenyl derivative having the general formula:

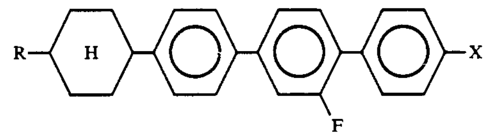

(I)

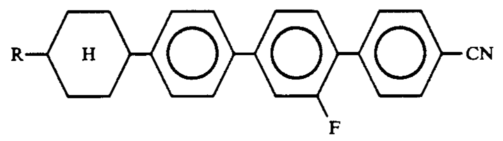

(I)

wherein R is a straight chain alkyl group having 1 to 12 carbon atoms and the cyclohexane ring is a trans isomer.

7. The liquid crystal composition of claim 6, wherein the terphenyl derivative is present between 5 and 15 weight percent, based on the total weight of the composition.

8. The liquid crystal composition of claim 6, wherein R is a straight alkyl having 1 to 7 carbon atoms.

9. The liquid crystal composition of claim of claim 6, wherein the 2'-fluoro-4''-trans-cyclohexyl-terphenyl derivative is 4''-(trans-4'''-pentylcyclohexyl)-2'-fluoro-4-cyano-terphenyl.

10. The liquid crystal composition of claim 6, wherein the 2'-fluoro-4''-trans-cyclohexyl-terphenyl derivative is 4-cyano-2'-fluoro-4''-(trans-4'''-propylcyclohexyl)-terphenyl.

11. The liquid crystal composition of claim 6, wherein the 2'-fluoro-4''-trans-cyclohexyl-terphenyl derivative is 4-cyano-2'-fluoro-4''-(trans-4'''-butylcyclohexyl)-terphenyl.

* * * * *